United States Patent
Kato et al.

(10) Patent No.: US 7,612,123 B2
(45) Date of Patent: Nov. 3, 2009

(54) CYCLOHEXENE OXIDE COMPOUND HAVING CYCLOHEXYL GROUP OR LONG-CHAIN ALKYL GROUP, AND USE THEREOF

(75) Inventors: Hisao Kato, Aichi (JP); Yoji Horie, Aichi (JP); Hiroshi Sasaki, Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 11/664,503

(22) PCT Filed: Oct. 4, 2005

(86) PCT No.: PCT/JP2005/018325

§ 371 (c)(1),
(2), (4) Date: Apr. 3, 2007

(87) PCT Pub. No.: WO2006/038605

PCT Pub. Date: Apr. 13, 2006

(65) Prior Publication Data

US 2008/0108725 A1    May 8, 2008

(30) Foreign Application Priority Data

Oct. 4, 2004  (JP)  ............... 2004-291161
Oct. 4, 2004  (JP)  ............... 2004-291209

(51) Int. Cl.
  *C08G 65/08*  (2006.01)
  *C07D 303/04*  (2006.01)
  *C07D 303/02*  (2006.01)

(52) U.S. Cl. .............. 522/170; 522/168; 549/200; 549/512; 549/546

(58) Field of Classification Search ............. 522/170, 522/168; 549/546, 200, 512
See application file for complete search history.

(56) References Cited

U.S. PATENT DOCUMENTS 4,524,162 A * 6/1985 Domeier .............. 523/438

(Continued)

FOREIGN PATENT DOCUMENTS

JP  2-225580  9/1990

JP  02225580 A  * 9/1990
JP  10-156952  6/1998

(Continued)

OTHER PUBLICATIONS

Masatoshi Asami et al., "Kinetic Resolution of *CIS*-3-Alkylcyclohexene Oxide by a Chiral Lithium Amide—An Application to a Synthesis of Both Enantiomers of Isomenthone-," Heterocycles, Vo. 52, No. 3, 2000, pp. 1029-1032.
Supplementary European Search Report dated Apr. 3, 2008.

*Primary Examiner*—Gwendolyn Blackwell
*Assistant Examiner*—Michael Pepitone
(74) *Attorney, Agent, or Firm*—Kratz, Quintos & Hanson, LLP

(57) ABSTRACT

An object of the present invention is to provide a cyclohexene oxide compound that gives a cured resin having a low refractive index and excellent transparency, curability, mold release properties, and mechanical properties, and that can be used as a component of an actinic radiation curing composition and/or heat curing composition.

The present invention is a cyclohexene oxide compound having a cyclohexyl group or a long-chain alkyl group, represented by Formula (1) below

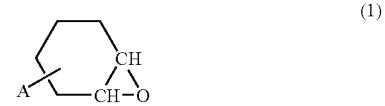

(1)

(in Formula (1), A denotes a cyclohexyl group, Formula (2) below, or an optionally branched alkyl group having 8 to 16 carbons)

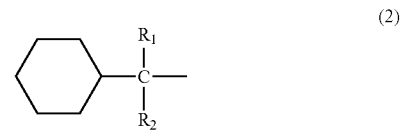

(2)

(in Formula (2), $R_1$ denotes a hydrogen atom or an optionally branched alkyl group having 1 to 4 carbons and $R_2$ denotes a hydrogen atom or an optionally branched alkyl group having 1 to 4 carbons).

4 Claims, 3 Drawing Sheets

U.S. PATENT DOCUMENTS

| | | | |
|---|---|---|---|
| 5,006,622 A * | 4/1991 | Kunzler et al. | 526/309 |
| 5,155,243 A * | 10/1992 | Fujiwa et al. | 549/546 |
| 5,270,418 A | 12/1993 | Kunzler et al. | |
| 5,705,316 A * | 1/1998 | Steinmann et al. | 430/269 |
| 6,319,652 B1 | 11/2001 | Akutsu et al. | 430/280.1 |
| 2002/0002212 A1 * | 1/2002 | Weinmann et al. | 522/148 |

FOREIGN PATENT DOCUMENTS

| | | |
|---|---|---|
| JP | 11-209326 | 8/1999 |
| JP | 2002-338659 | 11/2002 |
| JP | 2004-99467 | 4/2004 |
| WO | WO2004/035558 | 4/2004 |

* cited by examiner

CYCLOHEXENE OXIDE COMPOUND HAVING CYCLOHEXYL GROUP OR LONG-CHAIN ALKYL GROUP, AND USE THEREOF

TECHNICAL FIELD

The present invention relates to a novel cationically polymerizable cyclohexene oxide compound having a cyclohexyl group or long-chain alkyl group. Since actinic radiation curing and/or heat curing resins derived therefrom have a low refractive index and excellent transparency, curability, mold release properties, and mechanical properties, they can be used in mold release materials, paints, coating materials, adhesives, optical components, etc.

BACKGROUND ART

As epoxy compounds having a cyclohexene oxide structure, 3,4-epoxycyclohexylmethyl-3',4'-epoxycyclohexanecarboxylate (e.g. Celloxide 2021; manufactured by Daicel Chemical Industries, Ltd.), an adduct of 3,4-epoxycyclohexylmethyl-3',4'-epoxycyclohexanecarboxylate and ε-caprolactone (e.g. Celloxide 2081; manufactured by Daicel Chemical Industries, Ltd.), 1,2,8,9-diepoxylimonene (e.g. Celloxide 3000; manufactured by Daicel Chemical Industries, Ltd.), bis(3,4-epoxycyclohexylmethyl) adipate (e.g. UVR-6128; manufactured by Dow Chemical Japan), etc. are known.

Furthermore, an epoxy compound having a cyclohexene oxide structure but having no ester bond in the molecule, represented by Formula (3) below, has been reported (ref. e.g. Patent Publication 1 and Patent Publication 2).

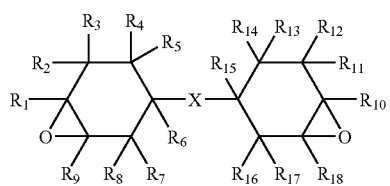

(3)

In Formula (3), X denotes an oxygen atom, a sulfur atom, —SO—, —SO$_2$—, —CH$_2$—, —C(CH$_3$)$_2$—, —CBr$_2$—, —C(CBr$_3$)$_2$—, —C(CF$_3$)$_2$—, —C(CCl$_3$)$_2$—, —CH(C$_6$H$_5$)—, or a single bond joining 2 alicycles, and R$_1$ to R$_{18}$ may be identical to or different from each other and are a hydrogen atom, a halogen atom, a hydrocarbon group optionally having an oxygen atom or a halogen atom, or an optionally substituted alkoxy group.

An example of production of a compound whose basic framework is represented by Formula (4) below (ref. e.g. Patent Publication 3) and the use thereof (ref. e.g. Patent Publication 4) have been reported. Here, a composition to which is added a thermocationic or photocationic polymerization initiator or an acid anhydride, and a mixture of this composition with another epoxy resin are reported. It is stated that these compositions may be used for sealing electronic components, as stabilizers for electrical insulating oil, and as an electrically insulating casting die.

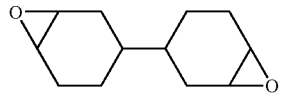

(4)

For use in an adhesive for a protective glass plate of an equimagnification photosensor, one represented by Formula (5) below has been cited as an example (n=1 to 20), and one represented by Formula (5) in which n=2 has been synthesized (ref. e.g. Patent Publication 5).

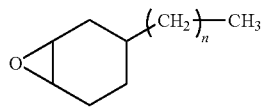

(5)

Several examples represented by Formula (5) in which n=0 or n=1 have also been reported.

As a starting material for the synthesis of 4-t-butyl-2-hydroxycyclohexyl methacrylate, one represented by Formula (6) below has been reported (ref. e.g. Patent Publication 6).

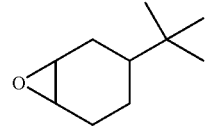

(6)

There is also a report on racemic forms of cis-3-t-butylcyclohexene oxide, cis-3-isopropylcyclohexene oxide, and cis-3-hexylcyclohexene oxide, and in this report these compounds were reduced to αβ unsaturated alcohols using an optically active lithium amide (ref. e.g. Non-Patent Publication 1)

None of these known publications describe the compound of the present invention, and specific examples of a synthetic method therefor are not described.

(Patent Publication 1) JP-A-10-156952 (JP-A denotes a Japanese unexamined patent application publication)
(Patent Publication 2) JP-A-2002-338659
(Patent Publication 3) JP-A-2004-99467
(Patent Publication 4) WO2004/035558
(Patent Publication 5) JP-A-02-225580
(Patent Publication 6) U.S. Pat. No. 5,270,418
(Non-Patent Publication 1) Masatoshi Asami et al., 'Kinetic resolution of cis-3-alkylcyclohexene oxide by a chiral lithium amide—an application to a synthesis of both enantiomers of isomenthone', HETEROCYCLES, 2000, Vol. 52, No. 2, p. 1029-1032

DISCLOSURE OF INVENTION

Problems to be Solved by the Invention

The present invention provides a cyclohexene oxide compound that gives a cured resin having a low refractive index and excellent transparency, curability, mold release properties, and mechanical properties, and that can be used as a component of an actinic radiation curing composition and/or heat curing composition.

Means for Solving the Problems

In order to solve the above-mentioned problems, the present inventors have carried out various investigations. As a result, it has been found that the problems can be solved by a cyclohexene oxide compound having a cyclohexyl group or a long-chain alkyl group, represented by Formula (1) below, and the present invention has thus been accomplished. That is, the present invention is (1) a cyclohexene oxide compound represented by Formula (1) below,

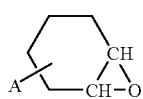
(1)

in Formula (1), A denotes a cyclohexyl group, Formula (2) below, or an optionally branched alkyl group having 8 to 16 carbons,

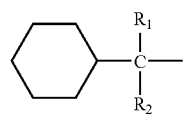
(2)

in Formula (2), $R_1$ denotes a hydrogen atom or an optionally branched alkyl group having 1 to 4 carbons, and $R_2$ denotes a hydrogen atom or an optionally branched alkyl group having 1 to 4 carbons, (2) an actinic radiation curing composition and/or heat curing composition comprising the above-mentioned cyclohexene oxide compound represented by Formula (1) and a cationic polymerization initiator, (3) a cured material formed by irradiating with actinic radiation and/or heating the curing composition according to (2) above, and (4) a process for producing a cyclohexene oxide compound represented by Formula (1).

The present invention is explained in detail below.

Effect of the Invention

In accordance with the present invention, a novel cyclohexene oxide compound having a cyclohexyl group or a long-chain alkyl group, represented by Formula (1), that can be synthesized from available starting materials, and a process for producing same are easily provided. A photocuring and/or heat curing resin derived from a composition comprising a cyclohexene oxide compound represented by Formula (1) has a low refractive index and excellent transparency, curability, mold release properties, and mechanical properties.

EXPLANATION OF REFERENCE NUMERALS AND SYMBOLS

Figure 1:
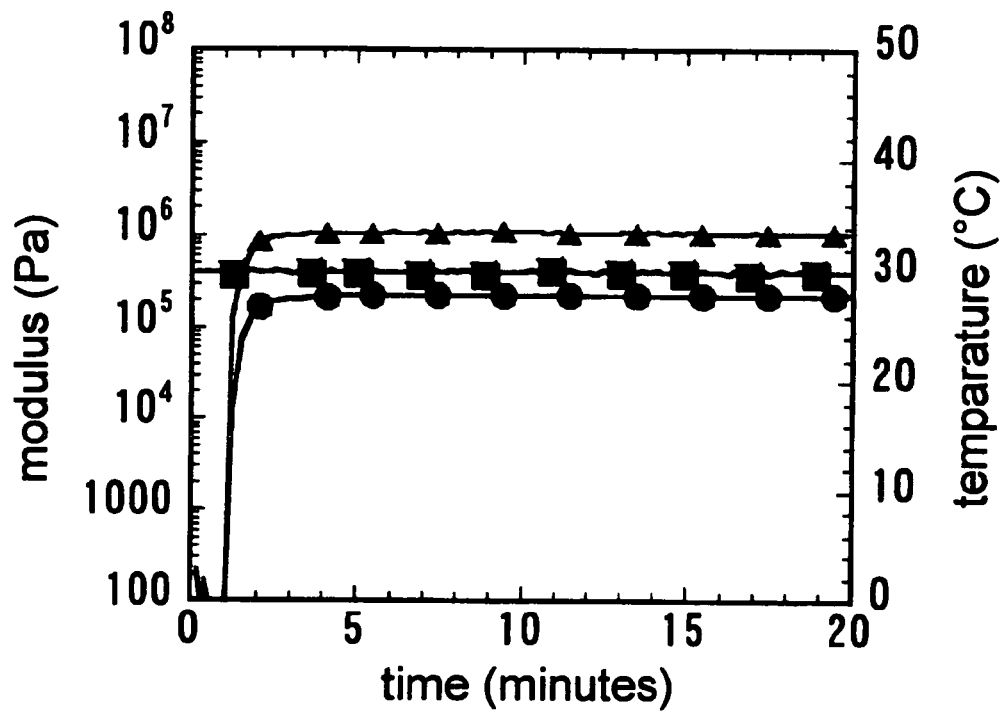
FIG. 1 shows the curability, storage modulus (G'), and loss modulus (G") of a photocuring composition comprising DoCHO.

In FIG. 1 to FIG. 5, the abscissa denotes measurement time (min).

In FIG. 1 to FIG. 5, the right ordinate denotes measurement of temperature (° C.).

In FIG. 1 to FIG. 5, the left ordinate denotes measurement of values (Pa) for storage modulus (G') and loss modulus (G").

In FIG. 1 to FIG. 5, '■' denotes the temperature in a measurement plate.

In FIG. 1 to FIG. 5, '●' denotes the storage modulus (G').

In FIG. 1 to FIG. 5, '▲' denotes the loss modulus (G").

Best Mode for Carrying out the Invention

The cyclohexene oxide compound of the present invention is represented by Formula (1). In Formula (1), A is a cyclohexyl group, Formula (2), or an optionally branched alkyl group having 8 to 16 carbons. In one aspect of the present invention, A in the cyclohexene oxide compound represented by Formula (1) of the present invention denotes a cyclohexyl group or Formula (2). In another aspect of the present invention, A in the cyclohexene oxide compound represented by Formula (1) of the present invention denotes an optionally branched alkyl group having 8 to 16 carbons.

Cyclohexene Oxide Compound having Cyclohexyl Group

The bonding position of a cyclohexyl group in the cyclohexene oxide compound represented by Formula (1) is the 3-position or the 4-position, and preferably the 4-position. In the case of Formula (2), the bonding position of Formula (2) in the cyclohexene oxide compound represented by Formula (1) is the 3-position or the 4-position, and preferably the 4-position.

$R_1$ of Formula (2) is a hydrogen atom or an optionally branched alkyl group having 1 to 4 carbons, preferably a hydrogen atom or a methyl group, and more preferably a methyl group. $R_2$ of Formula (2) is a hydrogen atom or an optionally branched alkyl group having 1 to 4 carbons, preferably a hydrogen atom or a methyl group, and more preferably a methyl group. $R_1$ and $R_2$ of Formula (2) may be identical to or different from each other, and are preferably identical to each other.

Specific examples of the cyclohexene oxide compound represented by Formula (1) include an epoxy compound represented by Formula (7) below and an epoxy compound represented by Formula (8) below.

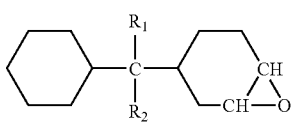
(7)

In Formula (7), $R_1$ is, a hydrogen atom or an optionally branched alkyl group having 1 to 4 carbons, and $R_2$ is a hydrogen atom or an optionally branched alkyl group having 1 to 4 carbons.

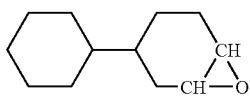
(8)

Production of Cyclohexene Oxide Compound having Cyclohexyl Group Represented by Formula (1)

The cyclohexene oxide compound represented by Formula (1) may be synthesized by, for example, epoxidizing a compound represented by Formula (9) below.

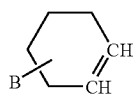
(9)

In Formula (9), B denotes a cyclohexyl group or Formula (2).

A compound represented by Formula (9) may be synthesized by, for example, dehydrating a compound represented by Formula (9) in which the double bond thereof is replaced by a single bond and a hydroxy group (a cyclohexanol having a cyclohexylmethyl group or a cyclohexyl group, etc.).

A synthetic example of the compound represented by Formula (9) is explained using a compound represented by Formula (7) in which $R_1$ and $R_2$ are both methyl groups. Compounds represented by Formula (7) in which $R_1$ and $R_2$ are hydrogen atoms or optionally branched alkyl groups having 1 to 4 carbons, compounds represented by Formula (8), etc. may be synthesized in a similar manner.

First, an olefin compound represented by Formula (10) is synthesized by subjecting a cyclohexanol having a cyclohexylmethyl group to a dehydration reaction using a catalyst. This synthesis may employ an aromatic solvent.

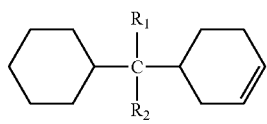
(10)

In Formula (10), $R_1$ is a hydrogen atom or an optionally branched alkyl group having 1 to 4 carbons, and $R_2$ is a hydrogen atom or an optionally branched alkyl group having 1 to 4 carbons.

The amount of catalyst used when synthesizing the olefin compound represented by Formula (10) is not particularly limited. The amount of catalyst depends on the type of catalyst, and is 0.001 to 1 times by mole relative to the OH group of the cyclohexanol, preferably 0.1 to 0.8 times, and more preferably 0.25 to 0.6 times. When the amount is less than 0.001 times, it might be difficult for the dehydration reaction to proceed, and when the amount exceeds 1 times, a side reaction might easily proceed, which is undesirable.

Examples of the catalyst used when synthesizing the olefin compound represented by Formula (10) include an alkali metal hydrogen sulfate and ammonium hydrogen sulfate. This catalyst may be used singly or in a combination of several types thereof. Potassium hydrogen sulfate and/or sodium hydrogen sulfate is preferably used as this catalyst.

As the aromatic solvent used when synthesizing the olefin compound represented by Formula (10), an aromatic solvent that forms an azeotrope with water, dichlorobenzene, etc. are preferable, and xylene, dichlorobenzene, ethylbenzene, etc. are suitably used.

The temperature at which the dehydration reaction of a cyclohexanol is carried out in the presence of a catalyst is preferably 80° C. to 250° C., more preferably 100° C. to 200° C., and particularly preferably 110° C. to 180° C.

The reaction time when synthesizing an olefin compound represented by Formula (10) depends on the type of catalyst, the amount thereof added, and the reaction temperature, but 1 to 30 hours is sufficient.

After this reaction is complete, for example, after the reaction mixture is filtered with a glass filter, the solvent is removed by vacuum distillation, and an olefin compound represented by Formula (10) may be obtained by silica gel column chromatography, vacuum distillation, etc.

Subsequently, the olefin compound represented by Formula (10) is epoxidized to give a cyclohexene oxide compound represented by Formula (1) of the present invention. A method for this epoxidation is not limited. For example, an olefin compound represented by Formula (10) and an organic peroxide are reacted. In this reaction, a halogen-containing solvent or an aromatic hydrocarbon solvent may be used.

The amount of organic peroxide when synthesizing the cyclohexene oxide compound represented by Formula (1) depends on the type of organic peroxide. For example, it is 1 to 2 times by mole relative to the double bond of the olefin compound represented by Formula (10), and preferably 1 to 1.2 times. When the amount of this catalyst is less than 1 times, the reaction might not proceed sufficiently, and when it exceeds 2 times, a side reaction might occur.

As a halogen-containing solvent used when epoxidizing an olefin compound represented by Formula (10), dichloromethane, 1,2-dichloroethane, chloroform, etc. may be used, and as an aromatic hydrocarbon solvent, benzene, toluene, xylene, etc. may suitably be used.

The temperature when synthesizing the cyclohexene oxide compound represented by Formula (1) from an olefin compound represented by Formula (10) and an organic peroxide is −30° C. to 40° C., preferably −10° C. to 30° C., and more preferably −5° C. to 20° C. When this reaction temperature is less than −30° C., it is difficult for a synthetic reaction to proceed, and when it exceeds 40° C., more impurities might be formed.

The reaction time depends on the type of organic peroxide, the amount thereof added, and the reaction temperature, but 1 to 30 hours is sufficient.

The cyclohexene oxide compound represented by Formula (1) after this reaction is complete may be purified by a standard purification method. For example, a saturated aqueous solution of sodium hydrogen carbonate is added to a reaction mixture, and an organic layer and an aqueous layer are separated by means of a separatory funnel. This organic layer is washed with, in sequence, a saturated aqueous solution of sodium hydrogen carbonate, a 10% aqueous solution of sodium thiosulfate, distilled water, and saturated brine, and dried over anhydrous sodium sulfate, etc. After the drying, filtration and removal of the solvent by vacuum distillation are carried out, and following this vacuum distillation is carried out to give a compound represented by Formula (1).

Cyclohexene Oxide Compound having Long-Chain Alkyl Group

The bonding position of the long-chain alkyl group in the cyclohexene oxide compound represented by Formula (1) is any one of the 1-position, the 3-position, and the 4-position, preferably the 3-position or the 4-position, and more preferably the 4-position. This long-chain alkyl group may be branched or straight chain. The number of carbons of the long-chain alkyl group is 8 to 16, and preferably 8 to 12.

The cyclohexene oxide compound represented by Formula (1) may be synthesized by any method. For example, the cyclohexene oxide compound represented by Formula (1) may be obtained by epoxidizing an olefin compound represented by Formula (11) below.

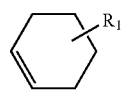

(11)

In Formula (11), $R_1$ denotes an optionally branched alkyl group having 8 to 16 carbons.

With regard to synthesis of the cyclohexene oxide compound represented by Formula (1) of the present invention, for example, a cyclohexanol having an optionally branched long-chain alkyl group is subjected to a dehydration reaction using a catalyst to synthesize an olefin compound represented by Formula (11). This reaction may employ an aromatic solvent.

The amount of catalyst used when synthesizing the olefin compound represented by Formula (11) is not particularly limited. The amount of catalyst depends on the type of catalyst, and is 0.001 to 1 times by mole relative to the OH group of the cyclohexanol having an optionally branched long-chain alkyl group, preferably 0.1 to 0.8 times, and more preferably 0.25 to 0.6 times. When the amount is less than 0.001 times, it might be difficult for the dehydration reaction to proceed, and when the amount exceeds 1 times, a side reaction might easily occur.

The catalyst used when synthesizing the olefin compound represented by Formula (11) is an alkali metal hydrogen sulfate, ammonium hydrogen sulfate, etc. This catalyst may be used singly or in a combination of several types thereof. Potassium hydrogen sulfate and/or sodium hydrogen sulfate is preferably used as this catalyst.

As the aromatic solvent used when synthesizing the olefin compound represented by Formula (11), an aromatic solvent that forms an azeotrope with water, dichlorobenzene, etc. are preferable, and xylene, dichlorobenzene, ethylbenzene, etc. are suitably used.

The temperature at which the dehydration reaction of a cyclohexanol having a long-chain alkyl group is carried out in the presence of a catalyst is preferably 80° C. to 250° C., more preferably 100° C. to 200° C., and particularly preferably 110° C. to 180° C.

The reaction time when synthesizing an olefin compound represented by Formula (11) depends on the type of catalyst, the amount thereof added, and the reaction temperature, but 1 to 30 hours is sufficient.

After this reaction is complete, for example, after the reaction mixture is filtered with a glass filter, the solvent is removed by vacuum distillation, and an olefin compound represented by Formula (11) may be obtained by silica gel column chromatography, vacuum distillation, etc.

Subsequently, the olefin compound represented by Formula (11) is epoxidized to give a cyclohexene oxide compound represented by Formula (1) of the present invention. A method for this epoxidation is not limited. For example, an olefin compound represented by Formula (11) and an organic peroxide are reacted. In this reaction, a halogen-containing solvent or an aromatic hydrocarbon solvent may be used.

The amount of organic peroxide when synthesizing the cyclohexene oxide compound represented by Formula (1) depends on the type of organic peroxide. For example, it is 1 to 2 times by mole relative to the double bond of the olefin compound represented by Formula (11), and preferably 1 to 1.2 times. When the amount of this catalyst is less than 1 times, the reaction might not proceed sufficiently, and when it exceeds 2 times, a side reaction might occur.

As a halogen-containing solvent used when epoxidizing an olefin compound represented by Formula (11), dichloromethane, 1,2-dichloroethane, chloroform, etc. may be used, and as an aromatic hydrocarbon solvent, benzene, toluene, xylene, etc. may suitably be used.

The temperature when synthesizing the cyclohexene oxide compound represented by Formula (1) from an olefin compound represented by Formula (11) and an organic peroxide is −30° C. to 40° C., preferably −10° C. to 30° C., and more preferably −5° C. to 20° C. When this reaction temperature is less than −30° C., it is difficult for a synthetic reaction to proceed, and when it exceeds 40° C., more impurities might be formed.

The reaction time depends on the type of organic peroxide, the amount thereof added, and the reaction temperature, but 1 to 30 hours is sufficient.

The cyclohexene oxide compound represented by Formula (1) after this reaction is complete may be purified by a standard purification method. For example, a saturated aqueous solution of sodium hydrogen carbonate is added to a reaction mixture, and an organic layer and an aqueous layer are separated by means of a separatory funnel. This organic layer is washed with, in sequence, a saturated aqueous solution of sodium hydrogen carbonate, a 10% aqueous solution of sodium thiosulfate, distilled water, and saturated brine, and dried over anhydrous sodium sulfate, etc. After the drying, filtration and removal of the solvent by vacuum distillation are carried out, and following this vacuum distillation is carried out to give a compound represented by Formula (1).

Cationic Polymerization Initiator

With regard to a cationic polymerization initiator that can be used for the composition of the present invention, any cationic polymerization initiator that is activated by irradiation with actinic radiation and can induce ring-opening of a ring-opening polymerizable group can be used. This is described in, for example, 'UV-EB Koka Zairyo (UV-EB Curing Materials)' (CMC Publishing Co., Ltd. (1992)). The actinic radiation referred to here means an electronic beam, ultraviolet radiation, visible light around 380 to 400 nm, etc.

Examples of UV cationic polymerization initiators include onium salts and organometallic complexes.

Examples of the onium salts include a diazonium salt, an iodonium salt, a sulfonium salt, a selenium salt, a pyridinium salt, a ferrocenium salt, a phosphonium salt, and a thiopyrylium salt, but onium salt initiators such as an aromatic iodonium salt and an aromatic sulfonium salt, which are relatively thermally stable, are preferably used. When an onium salt initiator such as an aromatic iodonium salt or an aromatic sulfonium salt is used, examples of the counteranion include $BF_4^-$, $AsF_6^-$, $SbF_6^-$, $PF_6^-$, and $B(C_6F_5)_4^-$. Furthermore, examples of the organometallic complexes include an iron-allene complex, a titanocene complex, and an arylsilanol-aluminium complex. For example, Optomer SP-150 (product name, manufactured by Asahi Denka Co., Ltd.), Optomer SP-170 (product name, manufactured by Asahi Denka Co., Ltd.), UVE-1014 (product name, manufactured by General Electric Company), CD-1012 (product name, manufactured by Sartomer), etc. can also be used.

A photosensitizer is used as necessary in combination with the photopolymerization initiator. Examples of the photosensitizer include ethyl N,N-dimethylaminobenzoate, isoamyl N,N-dimethylaminobenzoate, triethylamine, and triethanolamine.

A thermo-latent cationic polymerization initiator that can be used in the heat curing composition of the present invention is activated by heating and induces ring-opening of a ring-opening polymerizable group of an epoxy compound, an oxetane compound, etc.; examples thereof include various types of onium salts such as a tertiary ammonium salt, a phosphonium salt, and a sulfonium salt.

As the above-mentioned onium salt, a commercial compound may be used, such as, for example, Adekaopton CP-66 and Adekaopton CP-77 (product names, manufactured by Asahi Denka Co., Ltd.), San-aid SI-60L, San-aid SI-80L, and San-aid SI-100L (product names, manufactured by Sanshin Chemical Industry Co., Ltd.), or the CI series (manufactured by Nippon Soda Co., Ltd.).

Actinic Radiation Curing Composition

An actinic radiation curing composition may be obtained by mixing a compound represented by Formula (1) and a cationic polymerization initiator. In this case, the proportion of the cationic polymerization initiator is preferably in the range of 0.01 to 5 parts by mass relative to 100 parts by mass of the compound that is cured by actinic radiation, more preferably 0.1 to 4 parts by mass, and particularly preferably 1 to 3 parts by mass. When the proportion of this latent cationic polymerization initiator is less than 0.01 parts by mass, even if it is activated by the action of actinic radiation, a ring-opening reaction of a ring-opening polymerizable group might not proceed sufficiently, and when it exceeds 5 parts by mass, the effect in promoting polymerization will not be increased further, which is economically disadvantageous.

Irradiation with Actinic Radiation

The composition of the present invention may be cured by irradiation with actinic radiation. When polymerization is carried out by irradiation with actinic radiation, the light source that can be used is not particularly limited. As this light source, one having a light energy distribution at a wavelength of 400 nm or less may be used, such as, for example, a low pressure mercury lamp, a medium pressure mercury lamp, a high pressure mercury lamp, a super high pressure mercury lamp, a fluorescent lamp, a black light lamp, a microwave-excited mercury lamp, or a metal halide lamp. The irradiation strength on the composition is controlled for each target product and is not particularly limited. For example, the light irradiation strength in a light wavelength region effective for activation of a cationic polymerization initiator (normally light at 300 to 420 nm is used although it depends on the photopolymerization initiator) is preferably 0.1 to 100 mW/cm$^2$. When the irradiation strength on the composition is less than 0.1 mW/cm$^2$, the reaction time becomes too long, and when it exceeds 100 mW/cm$^2$, the heat emitted from the lamp and the heat generated during polymerization of the composition might degrade the cohesive strength of a cured material obtained, or turn it yellow, or cause degradation of a support.

Heat Curing Composition

A heat curing composition may be obtained by mixing a compound represented by Formula (1) and a thermo-latent cationic polymerization initiator. In this case, the proportion of the cationic polymerization initiator is preferably in the range of 0.01 to 5 parts by mass relative to 100 parts by mass of the heat curing compound, more preferably 0.1 to 4 parts by mass, and particularly preferably 1 to 3 parts by mass. When the proportion of this latent cationic polymerization initiator is less than 0.01 parts by mass, even if it is activated by heating, a ring-opening reaction of a ring-opening polymerizable group might not proceed sufficiently, and when it exceeds 5 parts by mass, the effect in promoting polymerization will not be increased further, which is economically disadvantageous.

Curing by Heating

The heat curing composition of the present invention may be cured by heat. The temperature of this curing is preferably 50° C. to 300° C., more preferably 60° C. to 250° C., and particularly preferably 80° C. to 210° C.

The heating time may be determined while examining the state of cure of the heat curing composition of the present invention. Specifically, it is preferably 1 to 300 minutes, and more preferably 5 to 250 minutes.

When polymerization is carried out by heat, heating may be carried out by a generally known method, and conditions therefor, etc. are not particularly limited.

The composition of the present invention can give a cured material with increased strength by heating after curing with actinic radiation. It is also possible to increase the strength of a cured material by irradiating with actinic radiation a material that has been cured by heating. In this case, a method in which, after curing is carried out by irradiation with actinic radiation, further curing is carried out by heating is preferable.

Other Compound Added

The composition of the present invention may comprise another cationically polymerizable compound. As the other cationically polymerizable compound, a compound having an oxetanyl group, or an epoxy compound other than those represented by Formula (1) may be added.

As the compound having an oxetanyl group, there can be cited a compound having one oxetanyl group per molecule, a compound having two oxetanyl groups per molecule, a compound having three oxetanyl groups per molecule, a compound having four oxetanyl groups per molecule, etc.

Examples of the compound having one oxetanyl group per molecule include 3,3-dichloromethyloxetane, 3,3-dimethyloxetane, 3-hydroxymethyloxetane, 3-methyl-3-hydroxymethyloxetane, 3-ethyl-3-hydroxymethyloxetane, 3-ethyl-3-phenoxymethyloxetane, 3-n-propyl-3-hydroxymethyloxetane, 3-isopropyl-3-hydroxymethyloxetane, 3-n-butyl-3-hydroxymethyloxetane, 3-isobutyl-3-hydroxymethyloxetane, 3-sec-butyl-3-hydroxymethyloxetane, 3-tert-butyl-3-hydroxymethyloxetane, 3-(meth)allyloxymethyl-3-ethyloxetane, (3-ethyl-3-oxetanylmethoxy)methylbenzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3-oxetanylmethoxy)ethyl] phenyl ether, isobutoxymethyl (3-ethyl-3-oxetanylmethyl) ether, isobornyloxyethyl (3-ethyl-3-oxetanylmethyl) ether, isobornyl (3-ethyl-3-oxetanylmethyl) ether, 3-ethyl-3-(2-ethylhexyl)oxetane), ethyl diethylene glycol (3-ethyl-3-oxetanylmethyl) ether, dicyclopentadiene (3-ethyl-3-oxetanylmethyl) ether, dicyclopentenyloxyethyl (3-ethyl-3-oxetanylmethyl) ether, dicyclopentenyl (3-ethyl-3-oxetanylmethyl) ether, tetrahydrofurfuryl (3-ethyl-3-oxetanylmethyl) ether, tetrabromophenyl (3-ethyl-3-oxetanylmethyl) ether, 2-tetrabromophenoxyethyl (3-ethyl-3-oxetanylmethyl) ether, tribromophenyl (3-ethyl-3-oxetanylmethyl) ether, 2-tribromophenoxyethyl (3-ethyl-3-oxetanylmethyl) ether, 2-hydroxyethyl (3-ethyl-3-oxetanylmethyl) ether, 2-hydroxypropyl (3-ethyl-3-oxetanylmethyl) ether, butoxyethyl (3-ethyl-3-oxetanylmethyl) ether, pentachlorophenyl (3-ethyl-3-oxetanylmethyl) ether, pentabromophenyl (3-ethyl-3-oxetanylmethyl) ether, and bornyl (3-ethyl-3-oxetanylmethyl) ether; examples of the compound having two or more oxetanyl groups include carbonate bisoxetane, adipate bisoxetane, terephthalate bisoxetane, cyclohexanedicarboxylic acid bisoxetane, 3,7-bis(3-oxetanyl)-5-oxanonane, 3,3'-(1,3-(2-methylenyl) propanediylbis(oxymethylene))bis-(3-ethyloxetane), 1,4-bis [(3-ethyl-3-oxetanylmethoxy)methyl]benzene, bis(3-ethyl-3-oxetanylmethyl) ether), 1,2-bis[(3-ethyl-3-oxetanylmethoxy)methyl]ethane, 1,3-bis[(3-ethyl-3-oxetanylmethoxy)methyl]propane, ethylene glycol bis(3-ethyl-3-oxetanylmethyl) ether, dicyclopentenylbis(3-ethyl-3-oxetanylmethyl) ether, triethylene glycol bis(3-ethyl-3-oxetanylmethyl) ether, tetraethylene glycol bis(3-ethyl-3-oxetanylmethyl) ether, tricyclodecanediyldimethylene (3-ethyl-3-oxetanylmethyl) ether, trimethylolpropane tris(3-ethyl-3-oxetanylmethyl) ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl) ether, pentaerythritol tetrakis(3-ethyl-3-oxetanylmethyl) ether, polyethylene glycol bis(3-ethyl-3-oxetanylmethyl) ether, dipentaerythritol hexakis(3-ethyl-3-oxetanylmethyl) ether, dipentaerythritol pentakis(3-ethyl-3-oxetanylmethyl) ether, dipentaerythritol tetrakis(3-ethyl-3-oxetanylmethyl) ether, caprolactone-modified dipentaerythritol hexakis(3-ethyl-3-oxetanylmethyl) ether, caprolactone-modified dipentaerythritol pentakis(3-ethyl-3-oxetanylmethyl) ether, ditrimethylolpropane tetrakis(3-ethyl-3-oxetanylmethyl) ether, EO-modified bisphenol A bis(3-ethyl-3-oxetanylmethyl) ether, PO-modified bisphenol A bis(3-ethyl-3-oxetanylmethyl) ether, EO-modified hydrogenated bisphenol A bis(3-ethyl-3-oxetanylmethyl) ether, PO-modified hydrogenated bisphenol A bis(3-ethyl-3-oxetanylmethyl) ether, and EO-modified bisphenol F (3-ethyl-3-oxetanylmethyl) ether.

The compound having an oxetanyl group added to the composition of the present invention is preferably a compound having two oxetanyl groups, a compound having three oxetanyl groups, or a compound having four or more oxetanyl groups, etc.

As epoxy compounds other than those represented by Formula (1), various types of compounds may be used. Examples of epoxy compounds having one epoxy group include phenyl glycidyl ether, (3,4-epoxycyclohexyl)methyl alcohol, (3,4-epoxycyclohexyl)ethyltrimethoxysilane, phenyl glycidyl ether, and butyl glycidyl ether, and examples of epoxy compounds having two or more epoxy groups include dicyclopentadiene oxide, limonene dioxide, 4-vinylcyclohexene dioxide, 3,4-epoxycyclohexylmethyl-3',4'-epoxycyclohexanecarboxylate, di(3,4-epoxycyclohexyl) adipate, (3,4-epoxy-6-methylcyclohexyl)methyl-3,4-epoxy-6-methylcyclohexanecarboxylate, ethylene 1,2-di(3,4-epoxycyclohexanecarboxylic acid) ester, a bisphenol A epoxy resin, a halogenated bisphenol A epoxy resin, a bisphenol F epoxy resin, o-, m-, and p-cresol novolac epoxy resins, a phenol novolac epoxy resin, and a polyhydric alcohol polyglycidyl ether.

The epoxy compound added to the composition of the present invention preferably has two or more epoxy groups.

Other Components

The composition of the present invention may further comprise as necessary the following components.

(1) A powder-form reinforcing agent or filler, for example, a metal oxide such as aluminum oxide or magnesium oxide, a metal carbonate such as calcium carbonate or magnesium carbonate, a silicon compound such as diatomaceous earth, basic magnesium silicate, calcined clay, fine powdered silica, fused silica, or crystalline silica, a metal hydroxide such as aluminum hydroxide, others such as kaolin, mica, powdered quartz, graphite, and molybdenum disulfide and, moreover, a fibrous reinforcing agent or filler, for example, glass fiber, ceramic fiber, carbon fiber, alumina fiber, silicon carbide fiber, boron fiber, polyester fiber, polyamide fiber, etc. They may be added at 10 to 900 parts by mass relative to 100 parts by mass of the composition of the present invention.

(2) A flame retardant such as a bromine compound or triphenyl phosphate. They may be added at 0.1 to 20 parts by mass relative to 100 parts by mass of the composition of the present invention.

(3) Furthermore, in order to improve the properties of a resin in a molding, etc., various types of curable monomer, oligomer, and synthetic resin may be added. Examples thereof include a diluent for an epoxy resin such as a monoepoxy, a phenol resin, an alkyd resin, a melamine resin, a fluorine resin, a vinyl chloride resin, an acrylic resin, a silicone resin, and a polyester resin, and these may be used singly or in a combination of two or more types. The proportion of these resins is an amount that does not impair the original properties of the resin composition of the present invention, that is, it is preferably 50 parts by mass or less relative to 100 parts by mass of the composition of the present invention.

The composition of the present invention may comprise a colorant or a dye such as a pigment. For example, titanium dioxide, iron black, molybdenum red, Prussian blue, ultramarine, cadmium yellow, cadmium red, etc. may be added to the composition of the present invention.

With regard to means for mixing the composition of the present invention and optional components, there are mixing by means of a mixer; melt-kneading by means of hot-melt mixing, rolls, or a kneader; and mixing using an appropriate organic solvent, etc.

Application

Since the photocuring resin derived from the compound represented by Formula (1) of the present invention has a low refractive index and excellent transparency, curability, mold release properties, and mechanical properties, it can be used in a mold release material, paint, coating material, adhesive, optical component, etc.

EXAMPLES

The present invention is explained more specifically below by reference to Examples, but the present invention should not be construed as being limited to these Examples.

Example 1

Synthesis of 4-dodecyl-1-cyclohexene

A 1 L four-necked flask equipped with a mechanical stirrer, a thermometer, and a Dean-Stark water separator was charged with 4-n-dodecylcyclohexanol (0.372 mol), potassium hydrogen sulfate (0.187 mol), and xylene (100 g), and they were heated and refluxed for 16 hours. After completion of the reaction, the reaction mixture was filtered with a glass filter, the solvent was removed by vacuum distillation, and purification was carried out by silica gel column chromatography (silica gel 60 (70-230 mesh), manufactured by Merck Ltd., elution solvent: n-hexane). The reaction product thus obtained was subjected to vacuum distillation using a kugelrohr distillation apparatus at 130° C./30 Pa to give 68.32 g (73% yield) of 4-dodecyl-1-cyclohexene (Formula (12) below). The results of $^1$H-NMR of this product are shown below.

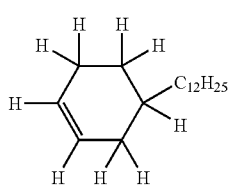

(12)

Results of Measurement of $^1$H-NMR (270 MHz, CDCl$_3$) δ (ppm); 0.63-2.20 (m, 32H), 5.58-5.81 (m, 2H)

It was determined from the results of the $^1$H-NMR that the compound thus obtained was 4-dodecyl-1-cyclohexene, which is represented by Formula (12).

Synthesis of 4-dodecyl-1,2-cyclohexene oxide (DoCHO)

A 2 L four-necked flask equipped with a mechanical stirrer and a thermometer was charged with a solution of the 4-dodecyl-1-cyclohexene (0.343 mol) synthesized above in dichloromethane (400 mL), which was cooled to 0° C. A solution of m-chloroperbenzoic acid (manufactured by Wako Pure Chemical Industries, Ltd., 0.412 mol) in dichloromethane (800 mL) was added thereto dropwise over 2 hours. During this addition, the temperature of the reaction mixture was maintained at 10° C. or less. After the dropwise addition of the solution of m-chloroperbenzoic acid in dichloromethane was complete, stirring was continued at 0° C. for a further 2 hours. After the reaction was complete, a saturated aqueous solution of sodium hydrogen carbonate (500 mL) was added dropwise to the reaction mixture while maintaining it at 10° C. or less. The solution was transferred to a separatory funnel, and the organic layer was separated. The aqueous layer obtained here was washed with dichloromethane (2×200 mL), and the dichloromethane wash was combined with the organic layer separated above.

Subsequently, this organic layer was washed using a separatory funnel with a saturated aqueous solution of sodium hydrogen carbonate (2×500 mL), a 10% aqueous solution of sodium thiosulfate (2×250 mL), distilled water (500 mL), and saturated brine (500 mL) in sequence. The organic layer was separated and dried over anhydrous sodium sulfate.

After drying, filtration was carried out, the solvent was removed from the filtrate by vacuum distillation, and 77.58 g (85% yield) of 4-dodecyl-1,2-cyclohexene oxide (Formula (13) below) was then obtained by vacuum distillation (108° C. to 123° C./30 Pa). Instrumental data such as $^1$H-NMR of this product are shown below.

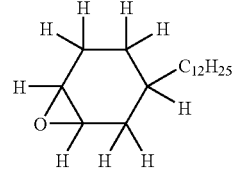

(13)

Results of Measurement of $^1$H-NMR (270 MHz, CDCl$_3$) δ (ppm); 0.57-2.26 (m, 32H), 3.02-3.28 (m, 2H) Viscosity: 44.5 mPa·s (25° C.) Refractive index: $n_D^{20}$ =1.476

It was determined from the results of the $^1$H-NMR, etc. that the compound thus obtained was 4-dodecyl-1,2-cyclohexene oxide, which is represented by Formula (13).

Example 2

Synthesis of 4-t-octyl-1-cyclohexene

A 1 L four-necked flask equipped with a mechanical stirrer, a thermometer, and a Dean-Stark water separator was charged with 4-t-octylcyclohexanol (0.471 mol), sulfuric acid (0.047 mol), sodium sulfate (0.047 mol), distilled water (35 g), and xylene (100 g), and they were heated and refluxed for 3 hours. After completion of the reaction, the reaction mixture was filtered with a glass filter, the solvent was removed by vacuum distillation, and purification was carried out by silica gel column chromatography (silica gel 60 (70-230 mesh), manufactured by Merck Ltd., elution solvent: n-hexane). The reaction product thus obtained was subjected to vacuum distillation using a kugelrohr distillation apparatus at 120° C./666 Pa to give 85.64 g (94% yield) of 4-t-octyl-1-cyclohexene (Formula (14) below). The results of $^1$H-NMR of this product are shown below.

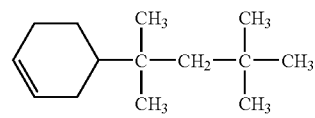

(14)

Results of Measurement of $^1$H-NMR (270 MHz, CDCl$_3$) δ (ppm); 0.83-1.49 (m, 19H), 1.71-2.16 (m, 5H), 5.60-5.77 (m, 2H)

It was determined from the results of the $^1$H-NMR that the compound thus obtained was 4-t-octyl-1-cyclohexene, which is represented by Formula (14).

Synthesis of 4-t-octyl-1.2-cyclohexene oxide (tOCE)

A 2 L four-necked flask equipped with a mechanical stirrer and a thermometer was charged with a solution of the 4-t-octyl-1-cyclohexene (0.346 mol) synthesized above in dichloromethane (400 mL), which was cooled to 0° C. A solution of m-chloroperbenzoic acid (manufactured by Wako Pure Chemical Industries, Ltd., 0.415 mol) in dichloromethane (800 mL) was added thereto dropwise over 2 hours. During this addition, the temperature of the reaction mixture was maintained at 10° C. or less. After dropwise addition of the solution of m-chloroperbenzoic acid in dichloromethane was complete, stirring was continued at 0° C. for a further 2 hours. After the reaction was complete, a saturated aqueous solution of sodium hydrogen carbonate (500 mL) was added dropwise to the reaction mixture while maintaining it at 10° C. or less. The solution was transferred to a separatory funnel, and the organic layer was separated. The aqueous layer obtained here was washed with dichloromethane (2×100 mL), and the dichloromethane wash was combined with the organic layer separated above.

Subsequently, this organic layer was washed using a separatory funnel with a saturated aqueous solution of sodium hydrogen carbonate (3×500 mL), a 5% aqueous solution of sodium thiosulfate (2×250 mL), distilled water (500 mL), and saturated brine (500 mL) in sequence. The organic layer was separated and dried over anhydrous sodium sulfate.

After drying, filtration was carried out, the solvent was removed from the filtrate by vacuum distillation, and 55.47 g (76% yield) of 4-t-octyl-1,2-cyclohexene oxide (Formula (15) below) was then obtained by vacuum distillation (67° C. to 77° C./30 Pa). Instrumental data such as $^1$H-NMR of this product are shown below.

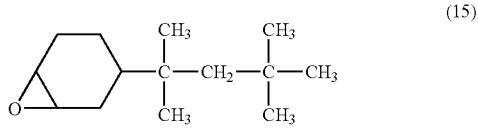
(15)

Results of Measurement of $^1$H-NMR (270 MHz, CDCl$_3$) δ (ppm); 0.63-2.24 (m, 24H), 3.02-3.26 (m, 2H) Viscosity: 11.8 mPa·s (25° C.) Refractive index: $n_D^{20}$ =1.475

It was determined from the results of the $^1$H-NMR, etc. that the compound thus obtained was 4-t-octyl-1,2-cyclohexene oxide, which is represented by Formula (15).

Example 3

Synthesis of 2-cyclohexyl-2-(3',4'-cyclohexenyl) propane

A 1 L four-necked flask equipped with a mechanical stirrer, a thermometer, and a Dean-Stark water separator was charged with 2-cyclohexyl-2-(4'-hydroxycyclohexyl)propane (0.446 mol), potassium hydrogen sulfate (0.089 mol), and xylene (100 g), and they were heated and refluxed for 16 hours. After completion of the reaction, the reaction mixture was filtered with a glass filter, the solvent was removed by vacuum distillation, and purification was carried out by silica gel column chromatography (silica gel 60 (70-230 mesh), manufactured by Merck Ltd., elution solvent: n-hexane). The reaction product thus obtained was subjected to vacuum distillation using a kugelrohr distillation apparatus at 150° C./1070 Pa to give 80.00 g (87% yield) of 2-cyclohexyl-2-(3',4'-cyclohexenyl) propane (Formula (16) below). The results of $^1$H-NMR of this product are shown below.

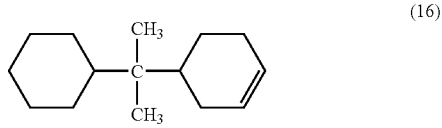
(16)

Results of Measurement of $^1$H-NMR (270 MHz, CDCl$_3$) δ (ppm); 0.71 (s, 3H), 0.75 (s, 3H), 0.85-2.17 (m, 18H), 5.59-5.77 (m, 2H)

It was determined from the results of the $^1$H-NMR that the compound thus obtained was 2-cyclohexyl-2-(3',4'-cyclohexenyl)propane, which is represented by Formula (16).

Synthesis of 2-cyclohexyl-2-(3',4'-epoxycyclohexyl) propane (CMECE)

A 2 L four-necked flask equipped with a mechanical stirrer and a thermometer was charged with a solution of the 2-cyclohexyl-2-(3',4'-cyclohexenyl)propane (0.36 mol) synthesized above in dichloromethane (400 mL), which was cooled to 0° C. A solution of m-chloroperbenzoic acid (manufactured by Wako Pure Chemical Industries, Ltd., 0.412 mol) in dichloromethane (800 mL) was added thereto dropwise over 2 hours. During this addition, the temperature of the reaction mixture was maintained at 10° C. or less. After dropwise addition of the solution of m-chloroperbenzoic acid in dichloromethane was complete, stirring was continued at 0° C. for a further 2 hours. After the reaction was complete, a saturated aqueous solution of sodium hydrogen carbonate (500 mL) was added dropwise to the reaction mixture while maintaining it at 10° C. or less. The solution was transferred to a separatory funnel, and the organic layer was separated. The aqueous layer obtained here was washed with dichloromethane (2×200 mL), and the dichloromethane wash was combined with the organic layer separated above.

Subsequently, this organic layer was washed using a separatory funnel with a saturated aqueous solution of sodium hydrogen carbonate (2×500 mL), a 10% aqueous solution of sodium thiosulfate (2×250 mL), distilled water (500 mL), and saturated brine (500 mL) in sequence. The organic layer was separated and dried over anhydrous sodium sulfate.

After drying, filtration was carried out, the solvent was removed from the filtrate by vacuum distillation, and 64.43 g (75% yield) of 2-cyclohexyl-2-(3',4'-epoxycyclohexyl)propane (CMECE, Formula (17) below) was then obtained by vacuum distillation (mainly a fraction at 96° C. to 98° C./25 Pa). Instrumental data such as $^1$H-NMR of this product are shown below.

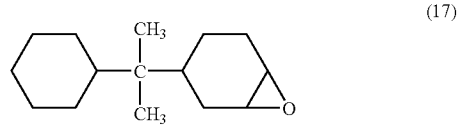
(17)

Results of Measurement of $^1$H-NMR (270 MHz, CDCl$_3$) δ (ppm); 0.59-0.74 (m, 6H), 0.79-2.25 (m, 18H), 3.01-3.28 (m, 2H) Viscosity: 51.8 mPa·s (25° C.) Refractive index: $n_D^{20}$ = 1.501

It was determined from the results of the $^1$H-NMR that the compound thus obtained was 2-cyclohexyl-2-(3',4'-epoxycyclohexyl)propane (CMECE), which is represented by Formula (17).

Example 4

Synthesis of 4-cyclohexyl-1-cyclohexene

A 1 L four-necked flask equipped with a mechanical stirrer, a thermometer, and a Dean-Stark water separator was charged with 4-cyclohexyl-1-cyclohexanol (0.549 mol), sulfuric acid (0.055 mol), sodium sulfate (0.055 mol), distilled water (40 g), and xylene (100 g), and they were heated and refluxed for 3 hours. After completion of the reaction, the reaction mixture was filtered with a glass filter, the solvent was removed by vacuum distillation, and purification was carried out by silica gel column chromatography (silica gel 60 (70-230 mesh), manufactured by Merck Ltd., elution solvent: n-hexane). The reaction product thus obtained was subjected to vacuum distillation using a kugelrohr distillation apparatus at 120° C./666 Pa to give 81.04 g (90% yield) of 4-cyclohexyl-1-cyclohexene (Formula (18) below). The results of $^1$H-NMR of this product are shown below.

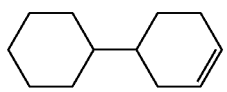

(18)

Results of Measurement of $^1$H-NMR (270 MHz, CDCl$_3$) δ (ppm); 0.85-2.14 (m, 18H), 5.53-5.74 (m, 2H)

It was determined from the results of the $^1$H-NMR that the compound thus obtained was 4-cyclohexyl-1-cyclohexene, which is represented by Formula (18).

Synthesis of 4-cyclohexyl-1,2-cyclohexene oxide (CCE)

A 2 L four-necked flask equipped with a mechanical stirrer and a thermometer was charged with a solution of the 4-cyclohexyl-1-cyclohexene (0.345 mol) synthesized above in dichloromethane (400 mL), which was cooled to 0° C. A solution of m-chloroperbenzoic acid (manufactured by Wako Pure Chemical Industries, Ltd., 0.415 mol) in dichloromethane (800 mL) was added thereto dropwise over 3 hours. During this addition, the temperature of the reaction mixture was maintained at 10° C. or less. After dropwise addition of the solution of m-chloroperbenzoic acid in dichloromethane was complete, stirring was further continued at 0° C. for 2 hours. After the reaction was complete, a saturated aqueous solution of sodium hydrogen carbonate (500 mL) was added dropwise to the reaction mixture while maintaining it at 10° C. or less. The solution was transferred to a separatory funnel, and the organic layer was separated. The aqueous layer obtained here was washed with dichloromethane (2×100 mL), and the dichloromethane wash was combined with the organic layer separated above.

Subsequently, this organic layer was washed using a separatory funnel with a saturated aqueous solution of sodium hydrogen carbonate (3×500 mL), a 5% aqueous solution of sodium thiosulfate (2×250 mL), distilled water (500 mL), and saturated brine (500 mL) in sequence. The organic layer was separated and dried over anhydrous sodium sulfate.

After drying, filtration was carried out, the solvent was removed from the filtrate by vacuum distillation, and 48.08 g (77% yield) of 4-cyclohexyl-1,2-cyclohexene oxide (CCE, Formula (19) below) was then obtained by vacuum distillation (mainly a fraction at 70° C./30 Pa). Instrumental data such as $^1$H-NMR of this product are shown below.

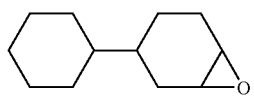

(19)

Results of Measurement of $^1$H-NMR (270 MHz, CDCl$_3$) δ (ppm); 0.78-2.22 (m, 18H), 3.04-3.25 (m, 2H) Viscosity: 8.3 mPa·s (25° C.) Refractive index: $n_D^{20}$ =1.492

It was determined from the results of the $^1$H-NMR that the compound thus obtained was 4-cyclohexyl-1,2-cyclohexene oxide (CCE), which is represented by Formula (19).

Example 5

Curing by Irradiation with Actinic Radiation 100 parts by mass of DoCHO and 2 parts by mass of UV9380C (bis(dodecylphenyl)iodonium hexafluoroantimonate, manufactured by GE Toshiba Silicones) were mixed well to give a photocuring composition. For comparison, 100 parts by mass of 3,4-epoxycyclohexylmethyl-3',4'-epoxycyclohexanecarboxylate (UVR-6110, manufactured by Dow Chemical Japan Co.) and 2 parts by mass of UV9380C were mixed well to give a comparative composition.

Figure 5:
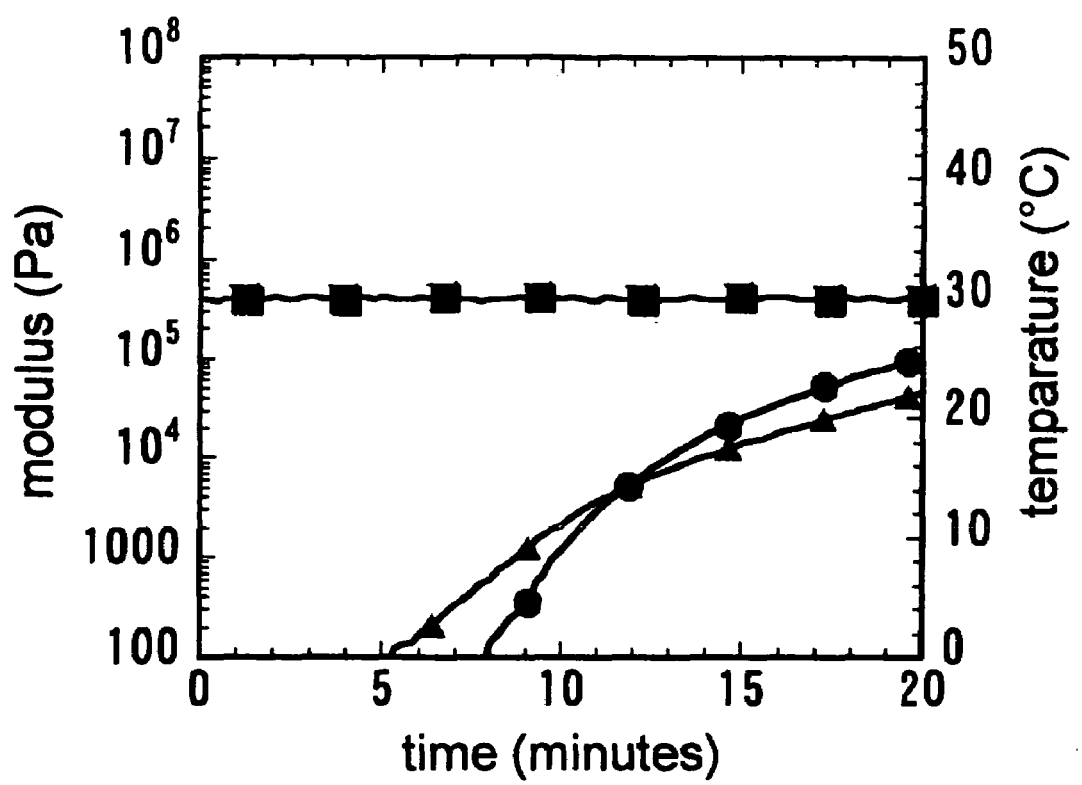
FIG. 5 shows the curability, storage modulus (G'), and loss modulus (G") of a composition comprising UVR-6110, which is a comparative composition.

With regard to these compositions, curability by irradiation with UV rays and the elastic modulus (storage modulus (G') and loss modulus (G")) were measured. The results of curability, etc. of the photocuring composition comprising DoCHO are shown in FIG. 1, and the results of curability, etc. of the comparative composition comprising UVR-6110 are shown in FIG. 5.

Figure 2:
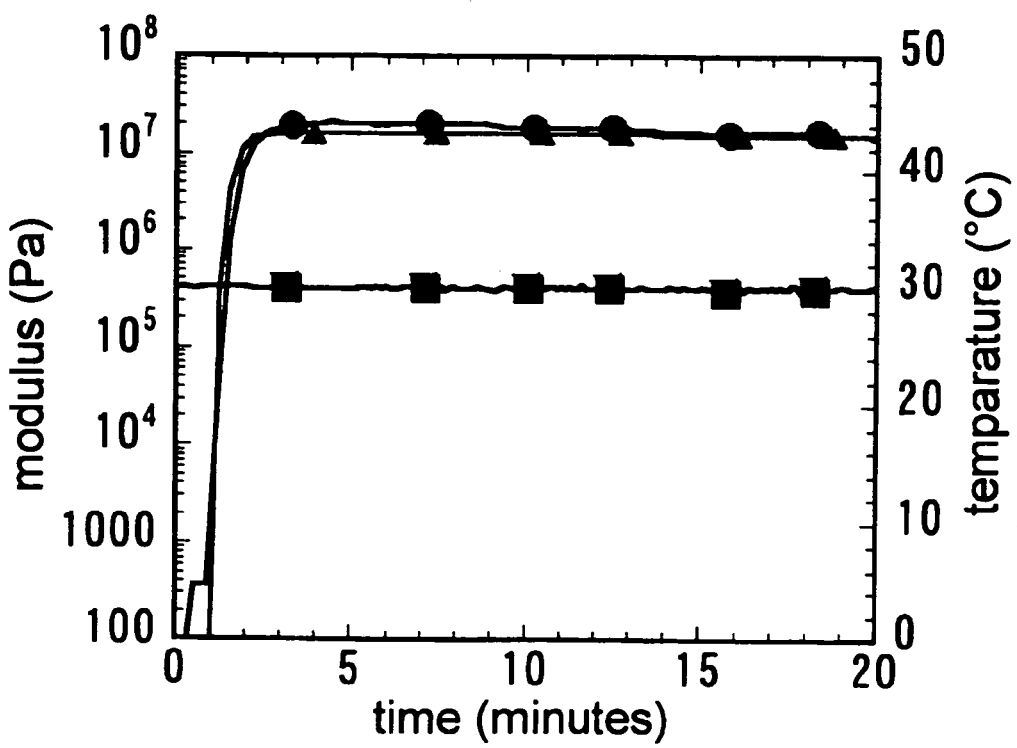
FIG. 2 shows the curability, storage modulus (G'), and loss modulus (G") of a photocuring composition comprising tOCE.
Figure 3:
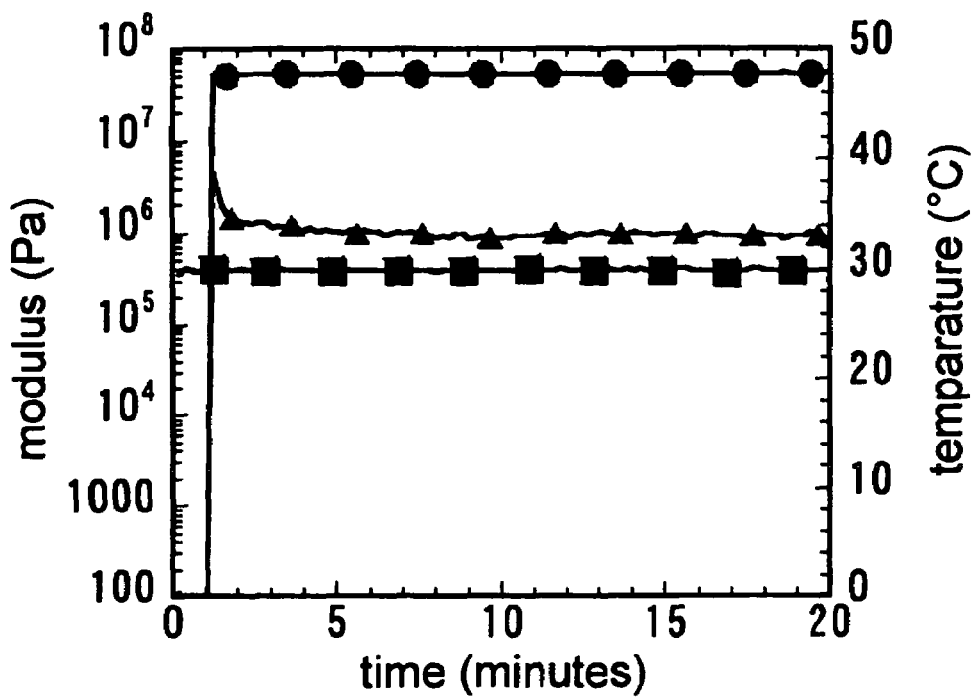
FIG. 3 shows the curability, storage modulus (G'), and loss modulus (G") of a photocuring composition comprising CMECE.
Figure 4:
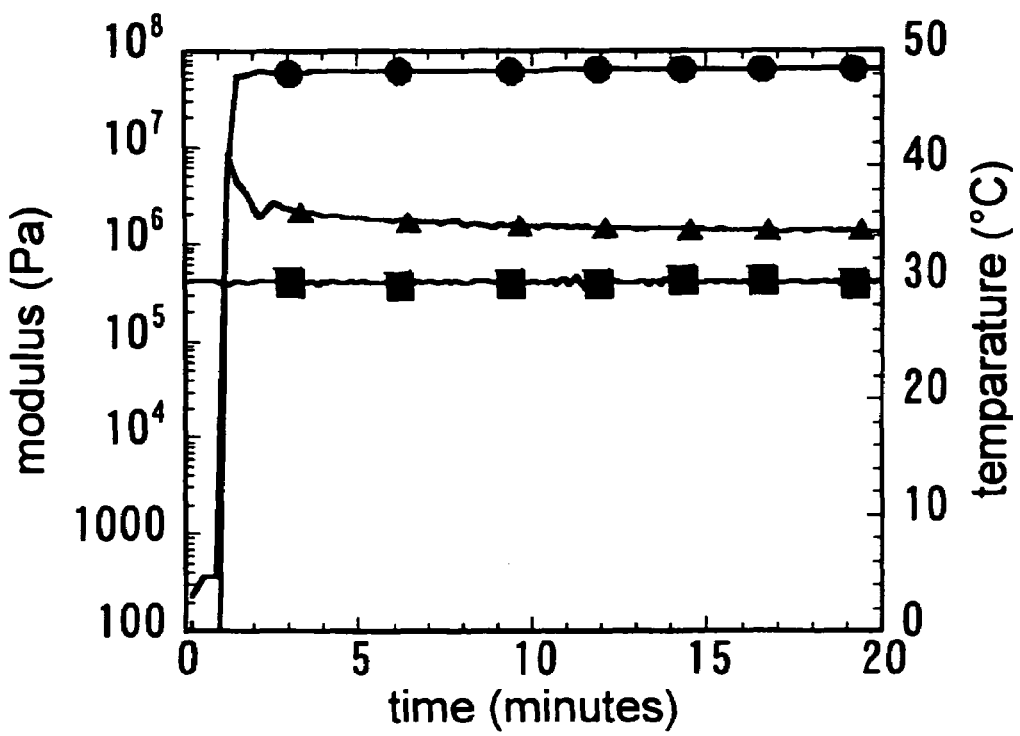
FIG. 4 shows the curability, storage modulus (G'), and loss modulus (G") of a photocuring composition comprising CCE.

Photocuring compositions were also prepared in the same manner except that tOCE, CMECE, and CCE were used instead of DoCHO. For these compositions, the curability by irradiation with UV rays and the elastic modulus (storage modulus (G') and loss modulus (G")) were also measured. The results of the composition comprising tOCE are shown in FIG. 2, the results of the composition comprising CMECE are shown in FIG. 3, and the results of the composition comprising CCE are shown in FIG. 4.

The abscissas of FIG. 1 to 5 denote measurement time, and irradiation with UV rays was started 1 minute after starting the measurement.

From the above-mentioned results, the photocuring compositions employing DoCHO, tOCE, CMECE, and CCE substantially completely cured immediately after irradiation with UV rays, and stable values were obtained for the storage modulus and the loss modulus. However, the comparative composition started to cure some time after starting irradiation, and did not cure 100% during the measurement time. Furthermore, the storage modulus and loss modulus of the comparative composition did not give stable values during the measurement time.

Irradiation conditions: mercury xenon lamp, irradiation intensity at 365 nm; 50 mW/cm$^2$.

Measurement time: 20 minutes

Viscoelasticity measurement conditions:

| | |
|---|---|
| temperature | 30° C. |
| frequency | 1 Hz |
| strain | 0.003 |
| gap | 500 μm |
| plate | P10ETC (diameter 10 mm) |

INDUSTRIAL APPLICABILITY

In accordance with the present invention, a novel cyclohexene oxide having a long-chain alkyl group, a cyclohexylmethyl group, or a cyclohexyl group can be synthesized from available starting materials, and a process for producing same can be provided. Since a photocuring and/or heat curing resin derived from a composition comprising an epoxy compound represented by Formula (1) has a low refractive index and excellent transparency, curability, mold release properties, and mechanical properties, it can be used in a mold release material, paint, coating material, adhesive, optical component, etc.

What is claimed is:

1. An actinic radiation curing composition and/or heat curing composition comprising a cyclohexene oxide compound represented by Formula (1) below and a cationic polymerization initiator,

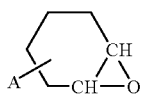
(1)

wherein A denotes a cyclohexyl group, Formula (2) below, or a branched alkyl group having 8 to 16 carbons,

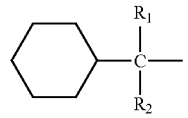
(2)

wherein $R_1$ denotes a hydrogen atom or an optionally branched alkyl group having 1 to 4 carbons and $R_2$ denotes a hydrogen atom or an optionally branched alkyl group having 1 to 4 carbons.

2. A cured material formed by irradiating with actinic radiation and/or heating the curing composition according to claim 1.

3. The actinic radiation curing composition according to claim 1, wherein the cationic polymerization initiator is a actinic radiation-latent cationic polymerization initiator.

4. The heat curing composition according to claim 1, wherein the cationic polymerization initiator is a thermo-latent cationic polymerization initiator.

* * * * *